United States Patent [19]

Frank

[11] Patent Number: 4,578,506

[45] Date of Patent: * Mar. 25, 1986

[54] PROCESS FOR THE PREPARATION OF TRIS(N-CARBALKOXYLAMINOMETHYL)-PHOSPHINE OXIDES AND SULFIDES

[75] Inventor: Arlen W. Frank, Slidell, La.

[73] Assignee: The United States of America as represented by the Secretary of Agriculture, Washington, D.C.

[*] Notice: The portion of the term of this patent subsequent to May 20, 1997 has been disclaimed.

[21] Appl. No.: 355,953

[22] Filed: Mar. 8, 1982

Related U.S. Application Data

[63] Continuation-in-part of Ser. No. 156,292, Jun. 4, 1980, abandoned, which is a continuation-in-part of Ser. No. 964,852, Nov. 29, 1978, Pat. No. 4,249,017.

[51] Int. Cl.$^4$ .............................. C07F 9/53; C07F 9/52
[52] U.S. Cl. ........................................ 560/148; 8/187; 544/186; 560/157; 560/158; 560/160
[58] Field of Search ................................. 560/148, 158

[56] References Cited

U.S. PATENT DOCUMENTS

| | | | |
|---|---|---|---|
| 3,159,667 | 12/1964 | Peters | 562/594 |
| 3,784,638 | 1/1974 | Lambert | 562/592 |
| 4,150,242 | 4/1979 | Wilson | 562/594 |
| 4,204,072 | 5/1980 | Frank | 560/158 |

Primary Examiner—Vivian Garner
Attorney, Agent, or Firm—M. Howard Silverstein; David G. McConnell; Raymond C. Von Bodungen

[57] ABSTRACT

The title compounds, having the formula $(RO_2CNHCH_2)_3PY$ where Y=oxygen or sulfur, are prepared by reacting a tetrakis(N-carbalkoxylaminomethyl)phosphonium salt having the formula $(RO_2CNHCH_2)_4P^+X^-$ with ammonia or a primary or secondary amine, followed by an oxidizing or sulfurizing agent. The products, after methylolation with formaldehyde, are useful as finishing agents for imparting flame retardant properties to cotton fabrics.

3 Claims, No Drawings

PROCESS FOR THE PREPARATION OF TRIS(N-CARBALKOXYLAMINOMETHYL)PHOSPHINE OXIDES AND SULFIDES

This is a continuation-in-part of Ser. No. 156,292, filed June 4, 1980, now abandoned, which is a continuation-in-part of Ser. No. 964,852, filed Nov. 29, 1978, now U.S. Pat. No. 4,249,017 which issued Feb. 3, 1981.

CROSS REFERENCE TO RELATED APPLICATIONS

Ser. No. 964,751, filed Nov. 29, 1978, now U.S. Pat. No. 4,204,072, "Tris(N-carbalkoxylaminomethyl)phosphines" by Arlen W. Frank, issued May 20, 1980.

Ser. No. 964,853, filed Nov. 29, 1978, now U.S. Pat. No. 4,171,448, "Quaternary Phosphonium Salts Bearing Carbamate Groups", by Arlen W. Frank, issued Oct. 16, 1979.

BACKGROUND OF THE INVENTION

1. Field of the Invention

This invention relates to tris(N-carbalkoxylaminomethyl)phosphine oxides and sulfides and to methods for preparing the same.

2. Description of the Prior Art

Nowhere in the prior art do there exist tertiary phosphine oxides and sulfides containing carbamate groups attached to each of the phosphorus substituents through its nitrogen atom.

Furthermore, the preparation and properties of such compounds, together with methods for their methylolation, and their application to cotton fabrics for the purpose of imparting flame retardant properties to the cotton, has not been known previously.

SUMMARY OF THE INVENTION

The instant invention relates to tris(N-carbalkoxylaminomethyl)phosphine oxides and sulfides having the formula $(RO_2CNHCH_2)_3PY$, where R is an alkyl radical having from 1 to 6 carbon atoms and Y is selected from the group of oxygen and sulfur, and the processes for producing said compounds.

It is the principal object of this invention to prepare tris(N-carbalkoxylaminomethyl)phosphine oxides and sulfides by methods which prevent interaction of products and by-products.

Other objects and improvements of this invention will become obvious from the description of the preferred embodiments.

DESCRIPTION OF THE PREFERRED EMBODIMENTS

The compounds of this invention have the general formula $(RO_2CNHCH_2)_3PY$, where R is an alkyl or substituted alkyl radical having from 1 to 6 carbon atoms, and Y is selected from the group of oxygen and sulfur.

In accordance with the practice of this invention, the compounds are prepared by:

(a) reacting a tetrakis(N-carbalkoxylaminomethyl)phosphonium salt having the formula $(RO_2CNHCH_2)_4P^+X^-$, where R is as defined above and X is an inorganic radical, with a base selected from the group consisting of ammonia, primary amines and secondary amines;

(b) treating the reaction mixture with an oxidizing or sulfurizing agent, and (c) recovering the product from the resulting mixture of products and by-products.

The tetrakis(N-carbalkoxylaminomethyl)phosphonium salts, themselves novel substances, are prepared by condensing an alkyl carbamate having the general formula $RO_2CNH_2$ with a tetrakis(hydroxymethyl)phosphonium salt having the general formula $(HOCH_2)_4P^+X^-$, where R and X are as defined above, in a molar ratio of at least 4:1, as described in U.S. Pat. No. 4,171,448. Examples of such substances are phosphonium salts in which R is methyl, ethyl, isopropyl, 2-methoxyethyl, n-butyl, and the like, and in which X is chloride, iodide, sulfate, and the like.

The bases employed in the practice of this invention comprise those substances capable of forming a salt with the acid HX, encompassing both inorganic and organic substances. The inorganic bases are exemplified by sodium hydroxide, barium hydroxide, sodium bicarbonate, disodium phosphate, trisodium phosphate, sodium sulfite, ammonium hydroxide, and the like. The organic bases are exemplified by triethylamine, morpholine, and the like. For reasons that are explained below, some of these bases, both inorganic and organic, are preferred to others.

The reaction between the tetrakis(N-carbalkoxylaminomethyl)phosphonium salt and the base, step (a), is most conveniently carried out in the presence of a solvent such as water or ethanol, but may also be performed in the absence of a solvent. The molar ratio may be varied from 3:1 to 1:20, the preferred ratio being from 1:1 to 1:2. The temperature may be varied from 0° to 150° C., depending on the strength of the base and the physical properties of the solvent. The pressure may be atmospheric, subatmospheric, or higher than atmospheric. If the product is air-sensitive, as is often the case with tertiary phosphines, the reaction may be carried out in an atmosphere of an inert gas, such as nitrogen or argon.

The hydrolysis of quaternary phosphonium salts to tertiary phosphines or their oxides by means of alkali is well known; see for example, L. Maier, "Organic Phosphorus Compound", G. M. Kosolapoff and L. Maier, eds., Wiley-Interscience, New York, 1972, Vol. 1, pp. 49–54. When this reaction is applied to tetrakis(N-carbalkoxylaminomethyl)phosphonium salts, however, the product is a mixture of tertiary phosphines containing little or none of the desired tris(N-carbalkoxylaminomethyl)phosphine. For example, the hydrolysis of tetrakis(N-carbomethoxylaminomethyl)phosphonium chloride, hereinafter referred to as TMPC, with aqueous sodium hydroxide gives the desired product, tris(N-carbomethoxylaminomethyl)phosphine, hereinafter referred to as TMP, as a water-insoluble solid in yields of 0 to 29%, depending on the reaction conditions (Table I). The major product is a water-soluble, liquid tertiary phosphine which cannot be induced to yield any TMP after work-up (nor any of the crystalline oxide, hereinafter referred to as TMPO, after oxidation). Barium hydroxide gives a 21% yield of TMP. Other moderately strong bases, such as sodium bicarbonate, disodium phosphate, trisodium phosphate or triethylamine, give yields in the 40 to 60% range, as does sodium hydroxide buffered with borax or phosphate. Yields of 87 to 92%, approaching the quantitative, are only attained with bases that are capable of reacting with formaldehyde (or formaldehyde derivatives), such as ammonium hydroxide, morpholine or sodium sulfite (Table I).

I suggest, without wishing to be bound by any specific hypothesis, that the preferred bases function by trapping the by-product alkyl N-methylenecarbamate, $RO_2CN=CH_2$, which is released in the hydrolysis of the phosphonium salt. Such a by-product is expected to be highly reactive, and capable of reacting either with the product, giving an N-substituted tertiary phosphine, or with water, giving an alkyl N-hydroxymethylcarbamate, $RO_2CNHCH_2OH$. The preferred bases could react directly with the alkyl N-methylenecarbamate giving products of the type $N(CH_2NHCO_2R)_3$ or $RO_2CNHCH_2SO_3Na$, or they could abstract formaldehyde from the alkyl N-hydroxymethylcarbamate giving products such as hexamethylenetetramine or the bisulfite addition compound of formaldehyde. In either event, the result would be the inactivation of the by-product, enabling the product to be recovered without hindrance.

TABLE I
HYDROLYSIS OF TMPC WITH VARIOUS BASES

| Example | Base | Conditions | TMP (% Yield) |
|---|---|---|---|
| 1 | NaOH | 100° C., 15 min | 29.1[a] |
| 2 | NaOH (borax) | 100° C., 15 min | 42.7 |
| 3 | NaOH (Na$_2$HPO$_4$) | 100° C., 15 min | 43.7 |
| 4 | NaOH (Na$_2$HPO$_4$) | 60° C., 90 min[b] | 45.0 |
| 5 | Ba(OH)$_2$[c] | 100° C., 1 hr | 21.0 |
| 6 | NaHCO$_3$ | 100° C., 1 hr | 60.1[d] |
| 7 | Na$_2$HPO$_4$ | 100° C., 1 hr | 60.3 |
| 8 | Na$_3$PO$_4$[c] | 100° C., 30 min | 48.2 |
| 9 | Triethylamine | 100° C., 30 min | 53.4 |
| 10 | Triethylamine | 25° C., 3 hr | 54.1[e] |
| 11 | Morpholine | 100° C., 1 hr | 46.7 |
| 12 | Morpholine | 25° C., 2 hr | 90.6[f] |
| 13 | NH$_4$OH | 25° C., 2 hr | 87.0 |
| 14 | Na$_2$SO$_3$ | 100° C., 1 hr | 92.5 |

[a]Yield raised to 51.3% by subsequent treatment with ammonium hydroxide (Example 15).
[b]Sodium hydroxide solution added dropwise to the buffered TMPC solution during the first 45 min.
[c]Mixture yellowed when the amount of base was doubled.
[d]Subsequent treatment with 6 N HCl regenerated only 24.4% of the TMPC.
[e]Yield unaffected by subsequent treatment with ammonium hydroxide or sodium bisulfite.
[f]Together with 93.5% yield of morpholine hydrochloride, mp 175-176° C. (lit. mp 175-176° C.).

The preferred bases are seen to fall into two categories. In the first category are substances which contain hydrogen attached to nitrogen, i.e. ammonia, primary, and secondary (but not tertiary) amines. When using bases in this category, an excess of the base should be employed to ensure that there is a sufficient quantity to react with both the by-product and the acid HX. The preferred molar ratio is therefore 1:2 or higher.

In the second category is sodium sulfite. When this base reacts with the acid HX, the base is transformed into sodium bisulfite, which is known to react with formaldehyde to give a crystalline adduct (J. F. Walker, "Formaldehyde", 3rd ed., Reinhold Publishing Corp., 1964, p. 251). In this case, no excess of base is necessary, and the preferred molar ratio is therefore 1:1.

Other categories will no doubt suggest themselves, to those skilled in the art, from among the many types of compounds that are capable of reacting with formaldehyde or formaldehyde derivatives (Walker, op. cit.).

The oxidizing agents employed in the practice of this invention comprise gases such as air, oxygen, oxides of nitrogen including nitric oxide and dinitrogen tetroxide, sulfur dioxide, and the like, inorganic substances such as hydrogen peroxide, mercuric oxide, potassium permanganate, chromic acid, and the like, and organic substances such as alkyl hydroperoxides, peroxy acids, diacyl peroxides, epoxides, ozonides, and the like.

The sulfurizing agents employed in the practice of this invention comprise elemental sulfur, inorganic substances such as sodium polysulfide, ammonium sulfide, mercuric sulfide, thiophosphoryl chloride, thiocyanogen, and the like, and organic substances such as mercaptans, episulfides, thionocarbonates, dialkyl disulfides, and the like.

The reaction between the tris(N-carbalkoxylaminomethyl)phosphine and the oxidizing or sulfurizing agent, step (b), is most conveniently carried out in the presence of a solvent such as water, ethanol or acetone but may also be performed in the absence of a solvent. The molar ratio may be varied from 10:1 to 1:10, the preferred ratio being 1:1. The temperature may be varied from 0° C. to 100° C., depending on the strength of the oxidizing or sulfurizing agent and the physical properties of the solvent. The pressure may be atmospheric, subatmospheric or higher than atmospheric. If the tertiary phosphine is air-sensitive, as is often the case, the reaction may be carried out in an atmosphere of an inert gas such as nitrogen or argon.

If the base used in the preparation of the tris(N-carbalkoxylaminomethyl)phosphine is a preferred base, i.e. a base capable of trapping the by-product formaldehyde or formaldehyde derivative, the tertiary phosphine need not be isolated and purified. In such a case, the oxidizing or sulfurizing agent can be added directly to the reaction mixture containing the base and the tertiary phosphine. The consequence is a considerable saving of time and effort. Illustrations of this technique are given in Examples 20-22.

If the base used in the preparation of the tris(N-carbalkoxylaminomethyl)phosphine is not a preferred base, as defined in the preceding paragraph, the subsequent oxidation or sulfurization yields a product distinctly different from that obtained through the use of a preferred base. This is illustrated in Example 23, where the base is sodium hydroxide. The product of Example 23 is a colorless oil, whereas that of Example 20, employing the same quaternary phosphonium salt, is a high-melting crystalline solid. Their spectra, solubility and other physical properties are also different. Efforts to interconvert the products by reaction of the crystalline product with methyl N-hydroxymethylcarbamate in the presence of sodium hydroxide catalyst, or by treatment of the liquid product with ammonium hydroxide, were not successful.

Melting points are corrected. Elemental analyses were preformed by commercial laboratories. IR spectra were taken on a Perkin-Elmer 137B with NACl optics (w=weak, m=medium, s=strong, vs=very strong). $^1H$ NMR spectra were taken on a Varian A-60, using TMS as an internal reference, and $^{31}P$ NMR spectra on a Varian HA-60-IL at 24.3 MHz, using 85% $H_3PO_4$ as an external reference (s=singlet, d=doublet, t=triplet, m=multiplet). Chemical shifts downfield of the reference are positive in both cases.

EXAMPLE 1

A slurry of 20.94 g (0.05 mol) of TMPC in 50 ml of water was treated dropwise, under a slow flow of argon gas, with a solution of 2.00 g (0.05 mol) of sodium hydroxide in 25 ml of water. During the addition, which took 15 min, the mixture cleared, turned milky, and cleared again. After heating at 100° C. for 15 min to complete the reaction, the solution, pH 8.4 and strongly positive to an iodine test for P(III), abruptly crystallized, giving 4.30 g (29.1% yield) of TMP, mp 82°–102° C. (sealed tube), identified by comparison of its infrared spectrum with that of the product of Example 13. The filtrate was extracted with chloroform, giving 16.49 g (65% yield) of a different tertiary phosphine, isolated as a colorless, neutral oil, $n_D^{20}$ 1.5011, soluble in water, acetone, and chloroform. IR (neat): 775m, 860w br, 1010 m, 1055w, 1145s, 1190s, 1250vs, 1530vs (NH, amide II), 1710vs (C=O, amide I), and 3350m br cm$^{-1}$.

EXAMPLES 2 to 4

Reaction of TMPC with sodium hydroxide in the presence of 0.01 mol of a buffer, following Example 1, gave crystalline TMP in 43 to 45% yield. The results are given in Table I, where the buffer is listed in brackets.

EXAMPLES 5 to 12

Reactions of TMPC with various other bases are summarized in Table 1. The procedure of Example 1 was followed in each experiment, using 0.05 mol of base unless otherwise stated. The yield of crystalline TMP varied from 40 to 60%.

EXAMPLE 13

Conc. ammonium hydroxide (10 ml) was added to a well-stirred slurry of 20.94 g (0.05 mol) of TMPC in 50 ml of water in an apparatus previously purged with argon. There was no exotherm nor gassing, but the mixture gradually thickened. After 30 min, more water (50 ml) was added to facilitate stirring. The mixture was then stirred for 2 hr, filtered, and the filter cake washed with water and dried in a vacuum desiccator, giving 12.85 g (87.0% yield) of TMP as a white, crystalline powder, mp 100°–125° C. All of these operations were performed under argon, for the product becomes hot and sticky when exposed to air. One recrystallization from 2-propanol raised the mp (sealed tube) to 137°–140° C. IR (Nujol): 768w, 777w, 848m, 962w, 1005m, 1140s, 1190m, 1235s, 1255vs, 1290s, 1420m, 1535vs br (NH, amide II), 1700vs and 1735s (C=O, amide I), and 3350m (NH) cm$^{-1}$. TMP is soluble in ethanol, chloroform and acetone, and insoluble in water, ether, carbon tetrachloride and benzene. It can be recrystallized from water (8 ml/g) or 2-propanol (7 ml/g).

EXAMPLE 14

A slurry of 20.94 g (0.05 mol) of TMPC in 50 ml of water was treated with 12.60 g (0.10 mol) of sodium sulfite, purged with argon, and heated at 100° C. for 1 hr, cooled and filtered, giving 13.66 g (92.5% yield) of crystalline TMP, mp 113°–119° C.

EXAMPLE 15

TMPC was hydrolyzed with sodium hydroxide as described in Example 1. After the completion of the reaction, the mixture was treated, without filtering, with 10 ml of conc. ammonium hydroxide and stirred overnight under argon. The yield of TMP, mp 107°–117° C., was 7.57 g (51.3%), consequently higher than in Example 1 but lower than in Example 13.

EXAMPLE 16

A solution of 400.0 g (0.464 mol) of octakis(N-carbomethoxylaminomethyl)diphosphonium sulfate, $[(CH_3O_2CNHCH_2)_4P^+]_2SO_4^=$, hereinafter referred to as OMPS, in 500 ml of water was purged with argon and treated with 200 ml of conc. ammonium hydroxide over a 15 min period at 21° to 26° C. Solids started to separate within minutes, and after 2 hr another 200 ml of water was added to facilitate stirring. After 4 hr, the product was collected on a filter, rinsed with water and dried, giving 280.0 g (102% yield) of crystalline TMP, mp 110°–115° C.

EXAMPLE 17

This example and the example which follows illustrate the preparation of TMPO from TMP.

A 30% solution of hydrogen peroxide (57.0 g, 0.5 mol) was added dropwise to a vigorously stirred slurry of 147.6 g (0.5 mol) of TMP in 500 ml of acetone under an argon atmosphere. Ice-bath cooling was applied as necessary to counter the strongly exothermic reaction. The TMP gradually dissolved, and was all in solution when two-thirds of the peroxide had been added. About 10 min. after the addition was completed, the product started to crystallize. Next day, the solid was collected on a filter, washed with acetone and dried, giving 98.9 g (63.5% yield) of TMPO, mp 179°–180° C. Work-up of the filtrate raised the yield to 126.0 g (81% yield). Two recrystallizations from ethanol afforded pure TMPO as a white, crystalline solid, mp 189°–190° C. IR (Nujol): 780m, 830w, 852m, 972w, 1015m, 1135m, 1145m, 1160m, 1190m, 1260s, 1300m, 1540s (NH, amide II), 1710vs br (C=O, amide I), 3250w (NH, bonded) and 3400w, (NH free) cm$^{-1}$. $^1$H NMR (DMSO-d$_6$): δ3.60 (s,CH$_3$), 3.47 (t, CH$_2$, J=9.0 Hz, blending into the CH$_3$ peak with D$_2$O; combined CH$_3$ and CH$_2$, 15H), and 7.34 (m, 3H, NH, vanishing with D$_2$O) ppm.

Anal. Calcd for C$_9$H$_{18}$N$_3$O$_7$P: C, 34.73; H, 5.83; N, 13.50; P, 9.95. Found: C, 34.69; H, 5.70; N, 13.48; P, 10.00.

The phosphine oxide TMPO is soluble in chloroform and insoluble in water, acetone, and the common organic solvents. It can be recrystallized from ethanol (25 ml/g) or water. When heated above its melting point, it gasses without discoloration and froths to a tan-colored resin at 260° C.

EXAMPLE 18

Hydrogen peroxide (30%) was added dropwise to a well-stirred slurry of 1476.2 g (5 mols) of TMP in 2000 ml of water under an argon atmosphere, with ice-bath cooling applied as needed to maintain the reaction temperature between 20° and 30° C. The addition was stopped after 3.5 hr, when 550.6 g (4.85 mols) of 30% hydrogen peroxide had been added. At this point, an iodine test for unreacted TMP was negative, and the product, which had separated during the reaction, abruptly foamed to the surface. The product was collected on a filter, rinsed with water and air-dried, giving 826.6 g (53.1% yield) of crystalline TMPO, mp 179°–180° C.

EXAMPLE 19

The example illustrates the preparation of tris(N-carbomethoxylaminomethyl)phosphine sulfide, (CH$_3$O$_2$CNHCH$_2$)$_3$PS, hereinafter referred to as TMPS, from TMP.

A mixture of 2.95 g (0.01 mol) of TMP, 0.32 g (0.01 g atom) of sulfur and 25 ml of benzene was heated to reflux (80° C.) under an argon atmosphere. After 1 hr, most of the solids had dissolved. The mixture was cooled and stripped of benzene under reduced pressure.

The residue was taken up in hot acetone, filtered hot to remove the unreacted sulfur (0.12 g), and stripped again under reduced pressure, leaving 2.40 g (73.4% yield) of TMPS as a white, crystalline solid. Two recrystallizations from ethanol afforded pure TMPS, mp 136.5°–137° C. IR (Nujol): 772w, 780w, 790w, 810w, 846m sh, 855s, 970m, 1015s br, 1145s, 1190s, 1240vs, 1290vs, 1520vs br (NH, amide II), 1710vs and 1740s (C=O, amide I), and 3400s (NH) cm$^{-1}$. $^1$H NMR (DMSO-d$_6$): δ3.61 (s, CH$_3$), 3.72 (t, CH$_2$, J=3.0 Hz, collapsing with D$_2$O to d, J=3.0 Hz; combined CH$_3$ and CH$_2$, 15H), and 7.39 (m, 3H, NH, vanishing with D$_2$O) ppm. $^{31}$P NMR (DMSO): δ48.5 ppm.

Anal. Calcd. for C$_9$H$_{18}$N$_3$O$_6$PS: C, 33.03; H, 5.54; N, 12.84; P, 9.46; S, 9.80. Found: C, 33.08; H, 5.49; N, 12.82; P, 9.60; S, 9.80.

The phosphine sulfide TMPS is soluble in chloroform, and insoluble in water or ethanol. It can be recrystallized from ethanol (6 ml/g), 2-propanol or water.

EXAMPLE 20

This example and the two which follow illustrate the use of a preferred base, ammonium hydroxide, in the preparation of TMPO or TMPS from TMPC or OMPS.

Conc. ammonium hydroxide (10 ml) was added to a well-stirred slurry of 20.94 g (0.05 mol) of TMPC in 100 ml of water in an apparatus previously purged with argon. The mixture gradually thickened. After 2 hr. the mixture, still containing the excess base and the by-products, was treated dropwise with 5.67 g (0.05 mol) of 30% hydrogen peroxide over a 20 min. period, with ice-bath cooling applied as needed to keep the temperature below 30° C. Next day, the mixture was stripped to dryness in a rotary evaporator, triturated with ethanol and filtered, giving 13.69 g (88.0% yield) of crystalline TMPO, mp 176°–178° C.

TMPC is not oxidized by hydrogen peroxide in the absence of a base.

EXAMPLE 21

An identical experiment in which the excess base and by-products were removed prior to oxidation gave 13.91 g (89.4% yield) of crystalline TMPO, mp 174°–177° C.

EXAMPLE 22

Conc. ammonium hydroxide (500 ml) was added to a solution of 1078.4 g (1.25 mol) of OMPS in 1500 ml of water in an apparatus previously purged with argon. TMP started to separate within minutes. After 2 hr. the mixture, still containing the excess base and the by-products, was treated dropwise with 977 g (2.87 mol) of 20% ammonium sulfide over a 2 hr. period at 25°–30° C. Next day, the product was collected on a filter, rinsed thoroughly with water and air-dried, giving 521.4 g of crude TMPS, mp 120°–125° C. One recrystallization from ethanol gave 398.3 g (48.9% yield) of crystalline TMPS, mp 132°–135° C.

EXAMPLE 23

This example illustrates the effect of using a base—sodium hydroxide, which is not one of the preferred bases—on the preparation of TMPO from TMPC.

A slurry of 20.94 g (0.05 mol) of TMPC in 50 ml of water was treated dropwise with a solution of 2.00 g (0.05 mol) of sodium hydroxide in 25 ml of water. During the addition, which took 5 min., the mixture cleared, turned milky, and cleared again. After 15 min. the solution was extracted with chloroform, and the chloroform extract filtered and stripped. The residue (16.79 g), a viscous, colorless oil which, unlike TMP, could not be induced to crystallize, was dissolved in 100 ml of acetone and treated dropwise with 5.70 g (0.05 mol) of 30% hydrogen peroxide over a 5 min period. The temperature rose to 40° C., and at the end an iodine test for unreacted tertiary phosphine was negative. The solution was stripped of acetone in a rotary evaporator, taken up in chloroform, extracted with water to remove any remaining peroxide, filtered, and stripped again, giving 14.00 g (62% yield) of the tertiary phosphine oxide as a colorless oil, n$_D^{20}$ 1.4962. IR (neat): 775w, 1005w br, 1055w, 1150m, 1190m, 1250s, 1290m sh, 1530s, (NH, amide II), 1710vs (C=O, amide I), and 3350m (NH) cm$^{-1}$. $^1$H NMR (CDCl$_3$): δ3.7–3.9 (m, 12H,CH$_3$), 3.9–4.6 (m, 8H, PCH$_2$), 6.63 (m, 2H, NH), and 8.13 (m, 1H, NH) ppm. $^{31}$P NMR (CHCl$_3$): δ45.3 ppm. The elemental analyses (N, 10.82; P, 5.98) clearly showed a 4:1 ratio of nitrogen to phosphorus, as opposed to 3:1 in TMPO.

The product was soluble in water, ethanol, acetone and chloroform, and insoluble in ether, carbon tetrachloride, ethyl acetate and benzene.

The foregoing examples are given to illustrate the preparation and properties of the compounds of this invention. The examples are given merely for purposes of illustration, and should not be construed as limiting the scope of the invention.

I claim:

1. A process for preparing tris(N-carbalkoxylaminomethyl)phosphine oxides and sulfides which comprises:
    (a) reacting a tetrakis(N-carbalkoxylaminomethyl)phosphonium salt having the formula (RO$_2$CNHCH$_2$)$_4$P$^+$X$^-$, where R is an alkyl radical having from 1 to 6 carbon atoms and X is an inorganic radical, with a base selected from the group consisting of ammonia, primary amines, and secondary amines, at a molar ratio of said phosphonium salt to base of at least 1:2 and a temperature of about 0° C. to 150° C.,
    (b) treating the reaction mixture at a temperature of about 0° C. to 100° C. with an agent selected from the group of oxidizing agents consisting of: air, oxygen, oxides of nitrogen, sulfur dioxide, hydrogen peroxide, mercuric oxide, potassium permanganate, chromic acid, and organic peroxides and epoxides or the group of sulfurizing agents consisting of: elemental sulfur, sodium polysulfide, ammonium sulfide, mercuric sulfide, thiocyanogen, and organic compounds selected from the group consisting of mercaptans, episulfides, thionocarbonates and dialkyl disulfides, and
    (c) recovering the product from the resulting mixture of products and by-products.

2. The process of claim 1 wherein the oxidizing agent is hydrogen peroxide.

3. The process of claim 1 wherein the sulfurizing agent is ammonium sulfide.

* * * * *